United States Patent [19]

Cotrel et al.

[11] Patent Number: 4,753,941

[45] Date of Patent: * Jun. 28, 1988

[54] AMIDES BASED ON CERTAIN 1,8-NAPHTYRIDINE-2-AMINES USEFUL AS ANXIOLYTICS

[75] Inventors: Claude Cotrel, Paris; Claude Guyon, Saint-Maur-Des-Fosses; Ge ard Roussel, Soisy-Sur-Seine; Ge ard Taurand, Creteil, all of France

[73] Assignee: Rhone-Poulenc Sante, Courbevoie, France

[*] Notice: The portion of the term of this patent subsequent to Feb. 10, 2004 has been disclaimed.

[21] Appl. No.: 2,996

[22] Filed: Jan. 13, 1987

[30] Foreign Application Priority Data

Jan. 16, 1986 [FR] France ............... 86 00554

[51] Int. Cl.$^4$ ............... A61K 31/435; C07D 471/04
[52] U.S. Cl. ............... 514/253; 514/300; 544/238; 544/405; 546/122
[58] Field of Search ............... 546/122; 544/238, 405; 514/253, 300

[56] References Cited

U.S. PATENT DOCUMENTS 4,642,308 2/1987 Cotrel et al. ............... 514/300

FOREIGN PATENT DOCUMENTS 1006725 4/1952 France .

*Primary Examiner*—Richard A. Schwartz

*Assistant Examiner*—Bernard I. Dentz

*Attorney, Agent, or Firm*—Stevens, Davis, Miller & Mosher

[57] ABSTRACT

The invention provides new substituted amides of formula

R—CONH—Het in which:
either R is phenyl substituted by acyloxy, alkylthio or alkyloxycarbonylamino, or by chloro at the 2- or 4-position, or by two alkyloxy radicals, or R is 2- or 4-pyridyl, pyrazinyl, 5,6-dihydrodithiin-2-yl, 5,6-dihydrooxathiin-2-yl, 1,3-dithiolyl, thiazolyl or substituted thienyl or furyl, or R is alkenyl (of 2 to 4 carbons) unsaturated in the α-position to the amide carbonyl, and Het is 1,8-naphthyridin-2-yl substituted at the 7-position by halogen, alkyloxy, phenoxy, 3-chloro- or dichlorophenoxy, hydroxy or cyano,
or R is methoxyphenyl and Het is 1,8-naphthyridin-2-yl substituted in the 7-position by 3-chloro- or dichlorophenoxy, hydroxy or cyano, or R is methoxy-3-pyridazinyl and Het is 1,8-naphthyridin-2-yl substituted at the 7-position by phenoxy, the said alkyl and acyl radicals containing 1 to 4 carbon atoms in a linear or branched chain, their preparation and the pharmaceutical compositions which contain them.

These new amides are useful as anxiolytics, hypnotics and muscle relaxants.

10 Claims, No Drawings

AMIDES BASED ON CERTAIN 1,8-NAPHTYRIDINE-2-AMINES USEFUL AS ANXIOLYTICS

This invention relates to substituted amides having pharmacological activity, to their preparation and to pharmaceutical compositions containing them. PCT Patent Application No. 84/00,489, describes benzamide derivatives of formula:

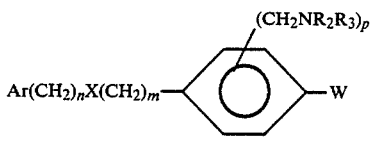

which are useful as antiarrhythmics.

Dutch Patent Application No. 73/05482 and U.S. Pat. No. 3,993,656 describe 1,8-naphthyridine derivatives of structure:

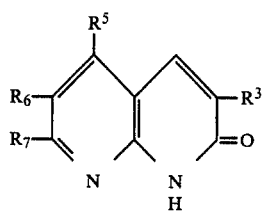

which are useful as bronchodilators and peripheral vasodilators or as hypotensive agents.

The present invention provides new substituted amides of formula:

in which either (A) R denotes phenyl substituted by acyloxy, alkylthio or alkyloxycarbonylamino, by chlorine in the 2- or 4-position or by two alkyloxy radicals, or R denotes a heterocyclic radical chosen from 2-pyridyl, 4-pyridyl, pyrazinyl, 5,6-dihydrodithiin-2-yl, 5,6-dihydrooxathiin-2yl, 1,3-dithiolyl or thiazolyl, or thienyl or furyl substituted by halogen or by alkylthio or R denotes alkenyl of 2 to 4 carbon atoms in which the double bond is in the α-position with respect to the carbonyl group of the amide function, and Het denotes 1,8-naphthyridin-2-yl substituted at the 7-position by halogen, alkyloxy, phenoxy, 3-chlorophenoxy, dichlorophenoxy, hydroxy or cyano, or (B) R denotes methoxyphenyl and Het denotes 1,8- naphthyridin-2-yl substituted at the 7-position by 3-chlorophenoxy, dichlorophenoxy, hydroxy or cyano; or R denotes methoxy-3-pyridazinyl and Het denotes 1,8-naphthyridin-2-yl substituted at the 7-position by phenoxy, the said alkyl and acyl radicals mentioned above containing 1 to 4 carbon atoms each in a linear or branched chain.

When the symbol Het contains a halogen substituent, the latter may be fluorine, chlorine or bromine.

When the symbol R contains a halogen substituent, the latter can also be fluorine, chlorine or bromine.

According to a feature of the invention, the amides of Formula (I) can be obtained by the action of an acid of formula:

in which R is as defined above, or a reactive derivative of this acid, on an amine of Formula:

in which Het is as defined above.

When the acid of formula (II) is employed, the reaction is preferably performed in the presence of a peptidecondensing agent such as a carbodiimide (e.g. dicyclohexylcarbodiimide) or N,N'-carbonyldiimidazole or 2-ethoxy-1-ethoxycarbonyl-1,2-dihydroquinoline, in an organic solvent such as an ether (e.g. tetrahydrofuran, dioxane, glyme, diglyme), an amide (e.g. dimethylformamide), a nitrile (e.g. acetonitrile) or a chlorinated solvent (e.g. methylene chloride, dichloroethane or chloroform), at a temperature between 0° C. and the refluxing temperature of the reaction mixture. The reaction is preferably performed at about 20° C.

When a reactive derivative of the acid of formula (II) is employed, it is possible to react the anhydride, a mixed anhydride, an acid halide or an ester [which can be chosen from the activated or unactivated esters of the acid of general formula (II)]. The reaction is then either performed in an organic medium, optionally in the presence of an acceptor for acid such as a nitrogenous organic base (e.g. a trialkylamine, a pyridine, 1,8-diazabicyclo[5.4.0]undec-7-ene or 1,5-diazabicyclo[4,3.0]non-5-ene), in a solvent such as is mentioned above, or a mixture of these solvents, at a temperature between 0° C. and the refluxing temperature of the reaction mixture, or performed in a two-phase aqueous organic medium in the presence of an alkali metal base or alkaline earth metal base (e.i. sodium hydroxide or potassium hydroxide) or an alkali metal carbonate or bicarbonate or alkaline earth metal carbonate or bicarbonate, at a temperature of between 0° and 40° C. It is also possible to work without a solvent at the melting point of the reaction mixture.

According to a further feature of the invention, the amides of formula (I), in which Het is 1,8-naphthyridin-2-yl substituted at the 7-position by hydroxy can also be prepared from the corresponding amide of formula (I) in which Het is 1,8-naphthyridin-2-yl substituted at the 7-position by a halogen atom (preferably a chlorine atom), by treatment in acid medium followed by hydrolysis of the product obtained.

The reaction is advantageously performed by treatment with acetic acid, optionally in the presence of acetic anhydride, or with formic acid, at a temperature between 50° C. and the refluxing temperature of the reaction mixture.

The acids of formula (II) and their reactive derivatives can be prepared by application of the methods described as follows (or by methods analogous to these methods) or according to the methods described below in the examples:

when R is acyloxyphenyl, according to von H. Schönenberger et al., Arz. Forsch., 14, 324 (1964);

when R is 5,6-dihydrodithiin-2-yl, according to K. G. Gundermann et al., 95, 2076 (1962);

when R is 1,3-dithiolyl, according to C. H. Pittman, J.C.S. Chem. Comm., 960 (1975);

when R is thiazolyl, according to H. Erlenmeyer et al., Helv. Chim. Acta, 20, 204 (1937) and 25, 1073 (1942);

when R is substituted thienyl, according to H. D. Hartough, The Chemistry of Heterocyclic compounds, thiophen and its derivatives, Interscience Publishers Inc., New York, p. 363 (1952);

when R is substituted furyl, according to the methods described in Advances in Het. Chem., -7, 377 (1966) and 30, 167 (1982).

The amines of formula (III) in which Het bears an alkyloxy or optionally substituted phenoxy substituent can be prepared from the corresponding amine in which the symbol Het beara a halogen substituent (preferably a chlorine atom), by the action of a hydroxyl derivative of formula:

R OH       (IV)

in which R' denotes an alkyl, phenyl, 3-chlorophenyl or dichlorophenyl radical, in basic medium, or by the action of the corresponding alcoholate.

The reaction is generally performed in the presence of a strong base (e.g. sodium hydroxide, potassium hydroxide, a quaternary ammonium hydroxide or sodium ethylate), at a temperature of between 50° and 150° C., or alternatively in the presence of the corresponding alcoholate (e.g. sodium alcoholate), in a solvent such as an amide (e.g. dimethylformamide) or an ether (e.g. tetrahydrofuran or dimethoxyethane), or without a solvent, in the presence of an excess of hydroxyl derivative at a temperature between 70° C. and the refluxing temperature of the reaction mixture.

When the alcoholate is used, the latter is obtained beforehand by the action of sodium on the alcohol of general formula (IV), at a temperature of between 20° and 80° C., or by the action of sodium hydride at a temperature of between 0° and 20° C. in a solvent such as dimethylformamide, dimethoxyethane or tetrahydrofuran. It is not necessary to isolate the alcoholate obtained in order to use it in the following reaction.

The amines of general formula (III) can also be prepared by application of the methods described below in the examples, or according to the method described by S. CARBONI, Gazz. Chim. Italiana, 96, 1456 (1966).

The amides of the present invention can be purified, there appropriate, by physical methods such as crystallization or chromatography.

The products of general formula (I) possess especially advantageous pharmacological properties. They show a high level of activity as anxiolytics, hypnotics and muscle relaxants demonstrated in the test mentioned below.

In particular, they possess high affinity in vitro for benzodiazepine receptors at concentrations of between 5 and about 1000 nM using the experimental technique described by J. C. Blanchard and L. Julou, J. of Neurochemistry, 40, 601 (1983), modelled on the work of Squires and Braestrup, Nature, 266, 732 (1977).

Furthermore, the new amides possess low toxicity: their oral LD$_{50}$ in mice is equal to or greater than 900 mg/kg.

Of special value are the amides of formula (I) in which: either R denotes phenyl substituted by acyloxy, alkylthio or alkyloxycarbonylamino, by chlorine in the 2- or 4-position, or by two alkyloxy radicals, or R denotes a heterocyclic radical chosen from 2-pyridyl, 4-pyridyl, pyrazinyl, 5,6-dihydrodithiin-2-yl, 5,6-dihydrooxathiin-2-yl, 1,3dithiolyl, thiazolyl, 2-thienyl and 2-furyl substituted by a halogen atom at the 5-position, or 5-alkylthio-2-thienyl, or R denotes alkenyl of 2 to 4 carbon atoms in which the double bond is in the α-position relative to the carbonyl group of the amide function, and Het denotes 1,8-naphthyridin-2-yl substituted at the 7-position by halogen, alkyloxy or phenoxy, or R denotes methoxyphenyl and Het denotes 1,8-naphthyridin-2-yl substituted at the 7-position by 3-chlorophenoxy, 3,4-dichlorophenoxy, hydroxy or cyano, or R denotes 6-methoxy-3-pyridazinyl and Het denotes 1,8-naphthyridin-2-yl substituted at the 7-position by phenoxy, the said alkyl and acyl radicals mentioned above containing 1 to 3 carbon atoms in a linear or branched chain.

Among these new amides, those which are of more special value are the substituted amides of formula (I) in which:

either R denotes phenyl substituted by an acyloxy radical or denotes a heterocyclic radical chosen from 5,6-dihydrodithiin-2-yl, 1,3-dithiolyl or 4-thiazolyl, and Het denotes 1,8-naphthyridin-2-yl substituted at the 7-position by halogen or methoxy, or R denotes 4-methoxyphenyl and Het denotes 1,8-naphthyridin-2-yl substituted at the 7-position with 3-chlorophenoxy or cyano.

The following products are especially valuable:

N-(7-chloro-1,8-naphthyridin-2-yl)-4-acetoxybenzamide

N-(7-chloro-1,8-naphthyridin-2-yl)-3-acetoxybenzamide

N-(7-methoxy-1,8-naphthyridin-2-yl)-3-acetoxybenzamide

N-(7-chloro-1,8-naphthyridin-2-yl)-1,3-dithiole-4-carboxamide

N-(7-cyano-1,8-naphthyridin-2-yl)-4-methoxybenzamide.

The examples which follow illustrate the present invention.

EXAMPLE 1

N,N'-Carbonyldiimidazole (14.7 g) is added to a solution of 4-chlorobenzoic acid (14.1 g) in anhydrous tetrahydrofuran (90 cc). The mixture is stirred for 1 hour at a temperature in the region of 20° C., until the evolution of gas has ceased. 2-Amino-7-chloro-1,8-naphthyridine (10.8 g) is then added and the mixture is heated under reflux for 3 hours.

The insoluble product is separated by filtration, washed with tetrahydrofuran (3×50 cc) and dried at 50° C. under reduced pressure (0.07 kPa). After recrystallization of the product thereby obtained in 2-propanol (100 cc), N-(7-chloro-1,8-naphthyridin-2-yl)-4-chlorobenzamide (9.3 g), m.p. 268° C., is obtained.

2-Amino-7-chloro-1,8-naphthyridine can be prepared according to the method described by S. CARBONI, Gazz. Chim. Italiana, 96, 1456 (1966).

EXAMPLE 2

N,N'-Carbonyldiimidazole (12.9 g) is added to a solution of 2-chlorobenzoic acid (12.5 g) in anhydrous tetrahydrofuran (250 cc). The mixture is stirred for 2 hours at a temperature in the region of 20° C., until the evolution of gas has ceased. 2-Amino-7-chloro-1,8-naphthyridine (8.9 g) is then added and the mixture is heated under reflux for 22 hours. The reaction mixture is poured into distilled water (2000 cc), and the precipitate formed is separated by filtration, washed with water and dried in the air. On recrystallization from ethanol (180 cc) of the product thereby obtained, N-(7-chloro-1,8-naphthyridin-2-yl)-2-chlorobenzamide (6.9 g), m.p. 180° C., is obtained.

EXAMPLE 3

4-Acetoxybenzoyl chloride (23.5 g) is added dropwise to a solution of 2-amino-7-chloro-1,8-naphthyridine (18 g) in anhydrous pyridine (215 cc), the temperature being maintained in the region of 20° C.

The reaction mixture is stirred for a further 1 hour at 20° C. and then poured into water (1200 cc). The precipitate obtained is separated by filtration, washed with water (300 cc) and dried in the air to give a solid (32.5 g), m.p. 220° C. On recrystallization in acetonitrile (400 cc) of some of the product (15.5 g) thereby obtained, N-(7-chloro-1,8-naphthyridin-2-yl)-4-acetoxybenzamide (11.4 g), m.p. 220° C., is obtained.

4-Acetoxybenzoyl chloride can be prepared according to the method described by von H. Schönenberger et al., Arz. Forsch. 14, 324 (1964).

EXAMPLE 4

The procedure is similar to that described in Example 3, but starting with 3-acetoxybenzoyl chloride (40.5 g), 2-amino-7-chloro-1,8-naphthyridine (32 g) and anhydrous pyridine (360 cc). After precipitation of the reaction mixture in water (2000 cc), washing with water (3×500 cc) and drying, a crystallized solid (58.8 g), m.p. approximately 195° C., is obtained. On recrystallization from acetonitrile (350 cc) of some of the product (12 g) thereby obtained, N-(7-chloro-1,8-naphthyridin-2-yl) -3-acetoxybenzamide (7.5 g), m.p. 207° C., is obtained.

3-Acetoxybenzoyl chloride can be prepared according to the method described by von H. Schönenberger et al., Arz. Forsch. 14, 324 (1964).

EXAMPLE 5

The procedure is similar to that described in Example 3, but starting with 2-amino-7-methoxynaphthyridine (3.5 g), 3-acetoxybenzoyl chloride (4.4 g) and anhydrous pyridine (40 cc). The reaction mixture is poured into water (400 cc) and the precipitate obtained is separated by filtration and then washed with water (6×100 cc) and dried in the air. On recrystallization from ethanol (140 cc) of the product thereby obtained, N-(7-methoxy-1,8-naphthyridin2-yl)-3-acetoxybenzamide (5.3 g), m.p. 172° C., is obtained.

2-Amino-7-methoxy-1,8-naphthyridine can be prepared according to the method described in U.S. Pat. No. 3,948,917.

EXAMPLE 6

The procedure is similar to that described in Example 2, but starting with 4-(methylthio)benzoic acid (20.7 g), N,N'-carbonyldiimidazole (25.1 g) and 2-amino-7-chloro-1,8-naphthyridine (27.8 g). The product obtained after precipitation of the reaction mixture in water and drying is purified by chromatography on a column 40 mm in diameter containing silica (300 g; 0.06 - 0.20 mm), eluting with a mixture (90:10 by volume) of methylene chloride and methylcyclohexane, and collecting 100-cc fractions. After concentration of fractions 15 to 44 to dryness at 40° C. under reduced pressure (4 kPa), a solid (8.9 g) is obtained which is recrystallized in ethyl acetate (550 cc). N-(7-Chloro-1,8-naphthyridin-2-yl)-4-(methylthio)benzamide (6.3 g), m.p. 199° C., is thereby obtained.

EXAMPLE 7

The procedure is similar to that described in Example 2, but starting with 3-ethoxycarbonylaminobenzoic acid (10 g), N,N'-carbonyldiimidazole (7.6 g) and 2-amino-7-methoxy-1,8-naphthyridine (5.95 g). The reaction mixture is then poured into water (1000 cc) and the precipitate formed is separated by filtration, washed with water (10 cc) and dried in the air. On recrystallization in ethyl acetate (100 cc) of the product thereby obtained, N-(7-methoxy-1,8-naphthyridin-2-yl)-3-ethoxycarbonylaminobenzamide (7.3 g), m.p. 120° C., is obtained.

3-Ethoxycarbonylaminobenzoic acid can be prepared in the following manner:

A mixture composed of 3-aminobenzoic acid (20 g), 1 M aqueous sodium bicarbonate solution (730 cc) and ethyl chloroformate (14 cc) is left with stirring for 30 minutes at 5° C. 2.5 N hydrochloric acid (300 cc) is then added to the reaction mixture. The precipitate formed is separated by filtration, washed with water (3×200 cc) and dried at 40° C. under reduced pressure (0.07 kPa). 3-Ethoxycarbonylaminobenzoic acid (25 g), m.p. 198° C., is thereby obtained.

EXAMPLE 8

The procedure is similar to that described in Example 2, but starting with 3,4-dimethoxybenzoic acid (14.6 g), N,N'-carbonyldiimidazole (12.9 g) and 2-amino-7-chloro-1,8-naphthyridine (8.9 g), and heating for 17 hours under reflux. The product obtained, after precipitation of the reaction mixture in water (1000 cc) and drying, is purified by recrystallization in acetonitrile (250 cc). N-(7-Chloro-1,8-naphthyridin-2-yl)-3,4-dimethoxybenzamide (8.5 g), m.p. 196° C., is thereby obtained.

EXAMPLE 9

The procedure is similar to that described in Example 2, but starting with 3,5-dimethoxybenzoic acid (14.56 g), N,N'-carbonyldiimidazole (12.9 g) and 2-amino-7-chloro-1,8-naphthyridine (8.9 g), and heating for 20 hours under reflux.

The product obtained after precipitation in water (2000 cc) and drying is purified by recrystallization in acetonitrile (900 cc). N-(7-Chloro-1,8-naphthyridin-2-yl) -3,5-dimethoxybenzamide (10.75 g), m.p. 235° C., is thereby obtained.

EXAMPLE 10

The procedure is similar to that described in Example 1, but starting with 1-pyridinecarboxylic acid (7.4 g), N,N'-carbonyldiimidazole (9.7 g) and 2-amino-7-chloro-1,8-naphthyridine (8.1 g), and performing the reaction for 18 hours at a temperature in the region of 25° C. The product obtained, after filtration, washing with tetrahydrofuran (60 cc) and water (120 cc) and then drying, is suspended in ethanol (120 cc) and stirred for 1 hour at 25° C. The insoluble product is separated by filtration and dried at 45° C. under reduced pressure (0.07 kPa). N-(7-Chloro-1,8-naphthyridin-2-yl)-2-pyridinecarboxamide (8.2 g), m.p. 319° C., is thereby obtained.

EXAMPLE 11

The procedure is similar to that described in Example 2, but starting with 4-pyridinecarboxylic acid (6.2 g), N,N'-carbonyldiimidazole (8.1 g) and 2-amino-7-chloro-1,8-naphthyridine (9 g). The product obtained, after precipitation in water (500 cc), washing with tetrahydrofuran (50 cc), then washing with water (200 cc) and drying (9.8 g; m.p. approximately 220° C.), is purified by crystallization in acetonitrile (850 cc). N-(7-Chloro-1,8-naphthyridin-2-yl)-4-pyridinecarboxamide (5.2 g), m.p. 228° C., is thereby obtained.

EXAMPLE 12

The procedure is similar to that described in Example 1, but starting with 2-pyrazinecarboxylic acid (7.5 g), N,N'-carbonyldiimidazole (9.7 g) and 2-amino-7-chloro-1,8-naphthyridine (10.8 g). The insoluble product is separated by filtration, washed with tetrahydrofuran (3×50 cc) and then with water (300 cc) and dried in the air. The product is suspended in acetonitrile (100 cc), stirred for 1 hour at 25° C. and separated by filtration, and then dried at 50° C. under reduced pressure (0.07 kPa). N-(7-Chloro-1,8-naphthyridin-2-yl)-2-pyrazinecarboxamide (11.75 g), m.p. 308° C., is thereby obtained.

EXAMPLE 13

A solution of 5,6-dihydro-1,4-dithiin-2-carbonyl chloride (14.3 g) in anhydrous pyridine (50 cc) is added in the course of 10 minutes at a temperature of 25° C. to a solution of 2-amino-7-chloro-1,8-naphthyridine (28.6 g) in anhydrous pyridine (300 cc). After 3 hours' stirring at a temperature of 25° C., the insoluble material is separated by filtration, and washed with pyridine (2×15 cc) and then isopropyl ether (20 cc). The filtrate is concentrated to dryness at 60° C. under reduced pressure (4 kPa) and the residue is taken up with water (200 cc). The crystallized solid obtained is separated by filtration, washed with water (200 cc) and dissolved in a chloroform/methanol (90:10 by volume) mixture (500 cc). The solution obtained is washed with 0.5 N hydrochloric acid solution (100 cc) and then water (3×100 cc), dried over sodium sulphate and concentrated to dryness at 60° C. under reduced pressure (4 kPa).

The solid obtained is purified by flash chromatography under 40 kPa on a column 63 mm in diameter containing silica (500 g; 0.04–0.06 mm), eluting with chloroform and collecting 300-cc fractions. After concentration of fractions 2 to 8 to dryness at 60° C. under reduced pressure (4 kPa), a solid (15 g) is obtained which is stirred in suspension in acetonitrile (325 cc) for 1 hour at 0° C. The insoluble product is separated by filtration, washed with acetonitrile (2×30 cc) and dried in the air. N-(7-Chloro-1,8-naphthyridin-2-yl)-5,6-dihydro-1,4-dithiin-2-carboxamide (11.9 g), m.p. 237° C., is obtained.

5,6-Dihydro-1,4-dithiin-2-carbonyl chloride can be prepared in the following manner:

A suspension of 5,6-dihydro-1,4-dithiin-2-carboxylic acid (13.1 g) in thionyl chloride (60 cc) is gradually heated to reflux. After 30 minutes under reflux, the solution obtained is concentrated to dryness at 50° C. under reduced pressure (4 kPa) and the oily residue obtained is washed with cyclohexane (2×100 cc). The decanted oil is dried at 50° C. under reduced pressure (4 kPa). 5,6-Dihydro-1,4-dithiin-2-carbonyl chloride (15.8 g) is thereby obtained, and this is used as it is in the following operation.

EXAMPLE 14

The procedure is similar to that described in Example 2, but starting with 5,6-dihydro-1,4-dithiin-2-carboxylic acid (10.9 g), N,N'-carbonyldiimidazole (10.9 g) and 2-amino-7-phenoxy-1,8-naphthyridine (11.9 g), and heating for 18 hours under reflux. The product obtained, after precipitation in water, washing with water and drying (18 g; m.p. approximately 240° C.), is purified by recrystallization in dimethylformamide (150 cc). N-(7-Phenoxy-1,8-naphthyridin-2-yl)-5,6-dihydro-1,4-dithiin-2carboxamide (15 g), m.p. 245° C., is thereby obtained.

5,6-Dihydro-1,4-dithiin-2-carboxylic acid can be prepared according to K. G. GUNDERMANN et al., Ber. 95, 2076 (1962).

EXAMPLE 15

The procedure is similar to that described in Example 2, but starting with 5,6-dihydro-1,4-oxathiin-2-carboxylic acid (7.3 g), N,N'-carbonyldiimidazole (9.7 g) and 2-amino-7-chloro-1,8-naphthyridine (7.2 g). The product obtained by precipitation in water is purified by recrystallization in dimethylformamide (60 cc). N-(7-Chloro-1,8-naphthyridin-2-yl)-5,6-dihydro-1,4-oxathiin-2-carboxamide (5.9 g), m.p. 270° C., is thereby obtained.

5,6-Dihydro-1,4-oxathiin-2-carboxylic acid can be prepared in the following manner:

Ethyl bromopyruvate (39 g) is added in the course of 20 minutes to a solution of 2-mercaptoethanol (15.6 g) in ethanol (50 cc). The reaction mixture is stirred for 2 hours and then concentrated to dryness under reduced pressure (4 kPa). The oily product obtained (37 g) is added to a mixture of 10 N sodium hydroxide (30 cc) and ethanol (170 cc). After 2 hours' heating under reflux, the reaction mixture is concentrated to dryness under reduced pressure (4 kPa), and then dissolved in distilled water (110 cc). The precipitate obtained after neutralization with concentrated hydrochloric acid (d=1.19) is separated by filtration, washed with distilled water (3×50 cc) and dried in the air. 5,6-Dihydro-1,4-oxathiin-2-carboxylic acid (10.8 g), m.p. 144° C., is obtained.

EXAMPLE 16

The procedure is similar to that described in Example 2, but starting with 1,3-dithiole-4-carboxylic acid (4.6 g), N,N'-carbonyldiimidazole (7.5 g) and 2-amino-7-chloro-1,8-naphthyridine (4.2 g). The product obtained by precipitation in water (4.8 g) is taken up with boiling acetonitrile (300 cc), the insoluble material is removed by filtration, and the filtrate is poured into water (500 cc). The precipitate obtained is purified by recrystallization in an acetonitrile/water (5:2 by volume) mixture (650 cc). N-(7-Chloro-1,8-naphthyridin-2-yl)- 1,3-dithiole-4-carboxamide (2.8 g), m.p. 235° C., is thereby obtained.

1,3-Dithiole-4-carboxylic acid can be prepared by application of the method described by C. U. Pittman Jr et al., J.C.S. Chem. Comm., 960 (1975).

EXAMPLE 17

The procedure is similar to that described in Example 2, but starting with 4-thiazolecarboxylic acid (4.8 g), N,N'-carbonyldiimidazole (7.5 g) and 2-amino-7-chloro-1,8-naphthyridine (4.8 g). The product obtained by precipitation in water is purified by recrystallization in dimethylformamide (350 cc). N-(7-Chloro-1,8-naphthyridin-2-yl)-4-thiazolecarboxamide (6 g), m.p. 325° C., is thereby obtained.

4-Thiazolecarboxylic acid can be prepared by application of the method described by H. Erlenmeyer et al., Helv. Chim. Acta, 25, 1073 (1942).

EXAMPLE 18

The procedure is similar to that described in Example 2, but starting with 5-thiazolecarboxylic acid (4.5 g), N,N'-carbonyldiimidazole (6.8 g) and 2-amino-7-chloro-1,8-naphthyridine (5 g). The product obtained by precipitation in water is purified by recrystallization in a dimethylformamide/acetonitrile (5:5 by volume) mixture (120 cc). N-(7-Chloro-1,8-naphthyridin-2-yl)-5-thiazolecarboxamide (5.5 g), m.p. 292° C., is thereby obtained.

5-Thiazolecarboxylic acid can be prepared by application of the method described by H. Erlenmeyer et al., Helv. Chim. Acta 20, 204 (1937).

EXAMPLE 19

The procedure is similar to that described in Example 2, but starting with 5-chloro-2-thiophenecarboxylic acid (9.5 g), N,N'-carbonyldiimidazole (9.5 g) and 2-amino-7-chloro-1,8-naphthyridine (8 g). The product obtained by precipitation in water is purified by recrystallization in propanol (700 cc). N-(7-Chloro-1,8-naphthyridin-2-yl)-5-chloro-2-thiophenecarboxamide (8.3 g), m.p. 275° C., is thereby obtained.

5-Chloro-2-thiophenecarboxylic acid can be prepared by application of the method described by L. Gattermann et al., Chem. Ber. 19, 688 (1886).

EXAMPLE 20

The procedure is similar to that described in Example 2, but starting with 5-methylthio-2-thiophenecarboxylic acid (5.6 g), N,N'-carbonyldiimidazole (5.2 g) and 2-amino-7-chloro-1,8-naphthyridine (4.3 g). The product obtained by precipitation in water is purified by recrystallization in a dimethylformamide/methanol (5:5 by volume) mixture (200 cc). N-(7-Chloro-1,8-naphthyridin-2-yl)-5-methylthio-2-thiophenecarboxamide (6.1 g), m.p. 235° C., is thereby obtained.

5-Methylthio-2-thiophenecarboxylic acid can be prepared by application of the method described by J. Cymerman-Craig et al., J. Chem. Soc., 237 (1954).

EXAMPLE 21

The procedure is similar to that described in Example 2, but starting with 5-bromo-2-furancarboxylic acid (2.9 g), N,N'-carbonyldiimidazole (2.4 g) and 2-amino-7-chloro-1,8-naphthyridine (1.8 g). The product obtained by precipitation in water is purified by recrystallization in a dimethylformamide/methanol (5:5 by volume) mixture (100 cc). N-(7-Chloro-1,8-naphthyridin-2-yl)-5-bromo-2-furancarboxamide (2.6 g), m.p. 285° C., is thereby obtained.

EXAMPLE 22

Acryloyl chloride (42 g) is added with stirring in the course of 30 minutes to a solution of 2-amino-7-chloro-1,8-naphthyridine (54 g) and triethylamine (115 g) in methylene chloride (1875 cc). The solution obtained is heated for 1 hour under reflux and then poured into isopropyl ether (5000 cc). The precipitate obtained is filtered off, washed with isopropyl ether (3×200 cc) and then water (3×200 cc) at 40° C. and dried in the air. The crude product obtained is purified by flash chromatography (under 50 kPa) on a column 60 mm in diameter containing silica (500 g; 0.04–0.06 mm), eluting with a mixture (99:1 by volume) of methylene chloride and methanol and collecting 100-cc fractions. After concentration of fractions 5 to 10 to dryness at 40° C. under reduced pressure (4 kPa), N-(7-chloro-1,8-naphthyridin-2-yl)acrylamide (5.85 g), m.p. 200° C., is obtained.

EXAMPLE 23

Methacryloyl chloride (9 g) dissolved in methylene chloride (30 cc) is added in the course of 20 minutes to a solution of 2-amino-7-chloro-1,8-naphthyridine (9 g) and triethylamine (19 g) in methylene chloride (300 cc). After 30 minutes' heating under reflux, the solution obtained is washed with 0.5 N hydrochloric acid (150 cc) and distilled water (2×150 cc) and then concentrated to dryness under reduced pressure (4 kPa). The solid obtained (13.5 g) is dissolved in boiling methanol (350 cc). After 3 hours' cooling at 4° C., the crystallized solid is separated by filtration, washed with methanol (2×30 cc) and dried in the air. The isolated product (9 g; m.p. 195° C.) is then added in the course of 5 minutes to concentrated sulphuric acid (d=1.83; 19 cc). The reaction mixture is heated for 10 minutes to 60° C., stirred for 1 hour at 25° C. and then poured into distilled water (200 cc). The precipitate formed is separated by filtration, washed with distilled water (5×20 cc) and recrystallized in acetonitrile (70 cc). N-(7-Chloro-1,8-naphthyridin-2-yl)methacrylamide (5.4 g), m.p. 182° C., is thereby obtained.

EXAMPLE 24

The procedure is similar to that described in Example 2, but starting with 4-methoxybenzoic acid (18.24 g), N,N'-carbonyldiimidazole (19.44 g) and 2-amino-7-(3-chlorophenoxy)-1,8-naphthyridine (20.6 g), heating for 2 hours under reflux.

The reaction mixture is poured into distilled water (1000 cc) and methylene chloride (1000 cc). The aqueous phase is extracted with methylene chloride (250 cc). The organic extracts are combined and then washed with distilled water (250 cc), dried over magnesium sulphate and concentrated to dryness at 50° C. under reduced pressure (4 kPa). The product obtained is purified by recrystallization in acetonitrile (700 cc). N-[7-(3-Chlorophenoxy)-1,8-naphthyridin-2-yl]-4-methoxybenzamide (20 g), m.p. 182° C., is thereby obtained.

2-Amino-7-(3-chlorophenoxy)-1,8-naphthyridine can be prepared in the following manner:

2-Amino-7-chloro-1,8-naphthyridine (17.95 g) is added to a mixture, preheated to 60° C., of 3-chlorophenol (51.4 g) and potassium hydroxide pellets (85% pure; 13.2 g). The reaction mixture is heated to 120° C. for 3 hours. The product is separated by filtration, washed with water to a pH of approximately 7 and then dried in the air. 2-Amino-7-(3-chlorophenoxy)-1,8-naphthyridine (20.6 g), m.p. 166° C., is obtained.

EXAMPLE 25

The procedure is similar to that described in Example 2, but starting with 4-methoxybenzoic acid (8.5 g), N,N'-carbonyldiimidazole (9 g) and 2-amino-7-(3,4-dichlorophenoxy)-1,8-naphthyridine (10.7 g). The product obtained by precipitation in water is purified by flash chromatography (under 30 kPa) on a column 40 mm in diameter containing silica (200 g; 0.04–0.06 mm), eluting with a mixture (9:1 by volume) of methylene chloride and methanol and collecting 100-cc fractions. After concentration of fractions 6 to 12 to dryness at 40° C. under reduced pressure (4 kPa), a solid (6.35 g) is obtained which is recrystallized in acetonitrile (160 cc). N-[7-(3,4-Dichlorophenoxy)-1,8-naphthyridin-2-yl]-4- methoxybenzamide (5.55 g, m.p. 180° C., is thereby obtained.

2-Amino-7-(3,4-dichlorophenoxy)-1,8-naphthyridine can be prepared in the following manner:

The procedure is similar to that described in Example 24, but starting with 2-amino-7-chloro-1,8-naphthyridine (17.95 g), 3,4-dichlorophenol (65.2 g) and potassium hydroxide pellets (85% pure; 13.2 g), heating to 125° C. for 22 hours. On recrystallization in acetonitrile (1500 cc) of the crude product obtained, 2-amino-7-(3,4-dichlorophenoxy)-1,8-naphthyridine (18 g), m.p. 206° C., is obtained.

EXAMPLE 26

The procedure is similar to that described in Example 1, but starting with 4-methoxybenzoic acid (8.2 g), N,N'-carbonyldiimidazole (8.7 g) and 2-amino-7-cyano-1,8-naphthyridine (6.9 g), and heating for 4 hours under reflux. The insoluble product is separated by filtration and the filtrate is poured into water (1000 cc). The resulting precipitate is filtered off, washed with water (3×75 cc) and dried in the air. The solid obtained is purified by flash chromatography (under 30 kPa) on a column 40 mm in diameter containing silica (170 g; 0.04–0.06 mm), eluting with pure methylene chloride and collecting 50-cc fractions. After concentration of fractions 5 to 27 to dryness at 40° C. under reduced pressure (4 kPa), the product obtained is purified by recrystallization in dioxane (160 cc). N-(7-Cyano-1,8-naphthyridin-2-yl)-4-methoxybenzamide (1.4 g), m.p. 283° C., is thereby obtained.

2-Amino-7-cyano-1,8-naphthyridine can be prepared according to the method described in Belgian Pat. No. 815,019.

EXAMPLE 27

The procedure is similar to that described in Example 2, but starting with 6-methoxy-3-pyridazinecarboxylic acid (2.2 g), N,N'-carbonyldiimidazole (2.3 g) and 2-amino-7-phenoxy-1,8-naphthyridine (2.7 g). The product obtained by precipitation in water is purified by recrystallization in acetonitrile (300 cc). N-(7-Phenoxy-1,8-naphthyridin-2-yl)-6-methoxy-3-pyridazinecarboxamide (3 g), m.p. 95° C., is thereby obtained.

6-Methoxy-3-pyridazinecarboxylic acid can be prepared by application of the method described by A. Pollak et al., Monatsh. Chem. 106, 473 (1975).

EXAMPLE 28

A solution of N-(7-chloro-1,8-naphthyridin-2-yl)-4-methoxybenzamide (5 g) in acetic acid (60 cc) and acetic anhydride (15 cc) is heated under reflux for 2 hours. The solution is cooled and poured into water (750 cc), the suspension obtained is alkalinized to pH 10 with 10 N sodium hydroxide and the solid is separated by filtration. After washing with water and acetone followed by drying at 50° C. under reduced pressure (0.07 kPa), N-(7-hydroxy- 1,8-naphthyridin-2-yl)-4-methoxybenzamide (4 g), m.p. approximately 346° C., is obtained.

N-(7-Chloro-1,8-naphthyridin-2-yl)-4-methoxybenzamide can be prepared in the following manner:

N,N'-Carbonyldiimidazole (4.9 g) is added to a solution of 4-methoxybenzoic acid (4.6 g) in anhydrous tetrahydrofuran (30 cc). An immediate evolution of gas is observed. The mixture is stirred for 1 hour at a temperature in the region of 20° C. until the evolution of gas has ceased. 2-Amino-7-chloro-1,8-naphthyridine (3.6 g) is then added and the mixture is heated under reflux for 18 hours.

The product obtained by precipitation in water (4.3 g; m.p. 208° C.) is dissolved in boiling acetonitrile (660 cc). After 3 hours' cooling at 4° C., the crystallized solid is separated by filtration, washed with acetonitrile (3×20 cc) and dried at 50° C. under reduced pressure (0.07 kPa). N-(7-Chloro-1,8-naphthyridin-2-yl)4-methoxybenzamide (3.5 g), m.p. 208° C., is obtained.

The present invention also provides pharmaceutical compositioos which contain a new amide of formula (I) in combination with a compatible and pharmaceutically acceptable adjuvant, diluent and/or coating. Theae compositions can be employed orally, rectally, parenterally or percutaneously.

As solid compositions for oral administration, tablets, pills, powders (generally in gelatin capsules) or granules may be used. In these compositions, the active product according to the invention is mixed with one or more inert diluents such as sucrose, lactose or starch. These compositions can also include substances other than diluents, e.g. a lubricant such as magnesium stearate.

As liquid compositions for oral administration, emulsions which are pharmaceutically acceptable, solutions, suspensions, syrups and elixirs containing inert diluents such as water or liquid paraffin may be used. These compositions can also include substances other than the diluents, e.g. wetting agents, sweeteners or flavourings.

The compositions according to the invention for parenteral administration can be aqueous or non-aqueous sterile solutions, suspensions or emulsions. As a solvent or vehicle, propylene glycol, a polyethylene glycol, vegetable oils, especially olive oil, or injectable organic esters, e.g. ethyl oleate, may be employed. These compositions can also contain adjuvants, especially wetting agents, emulsifiers and dispersants. The sterilization can be carried out in several ways, e.g. by means of a bacteriological filter, by incorporating sterilizing agents in the composition, by irradiation or by heating. They can also be prepared in the form of sterile solid compositions which can be dissolved at the time of use in sterile water or any other injectable sterile medium.

The compositions for rectal administration are suppositories which can contain, in addition to the active product, excipients such as cocoa butter or suppo-wax.

The compositions for percutaneous administration are creams, ointments, lotions and liniments, in which the active product is combined with liquid or pasty excipients, preferably in combination with a vehicle which promotes percutaneous migration.

The compositions according to the invention are especially useful in human therapy on account of their anxiolytic, hypnotic and muscle relaxant action.

In human therapy, the dose used depends on the effect sought and the length of the treatment; it is generally between 10 and 500 mg per day orally for an adult.

In general, the doctor will determine the dosage which he judges to be most suitable in relation to the age, weight and all other factors specific to the subject to be treated.

The examples which follow illustrate compositions according to the invention.

EXAMPLE A

Tablets containing 10-mg doses of active product and having the following composition are prepared according to the customary technique:

| | |
|---|---|
| N—(7-chloro-1,8-naphthyridin-2-yl)-3-acetoxybenzamide | 0.010 g |
| starch | 0.200 g |
| precipitated silica | 0.036 g |
| magnesium stearate | 0.004 g |

EXAMPLE B

Tablets containing 10-mg doses of active product and having the following composition are prepared according to the customary technique:

| | |
|---|---|
| N—(7-chloro-1,8-naphthyridin-2-yl)-1,3-dithiole-4-carboxamide | 0.010 g |
| starch | 0.200 g |
| precipitated silica | 0.036 g |
| magnesium stearate | 0.004 g |

EXAMPLE C

Tablets containing 10-mg doses of active product and having the following composition are prepared according to the customary technique:

| | |
|---|---|
| N—(7-cyano-1,8-naphthyridin-2-yl)-4-methoxybenzamide | 0.010 g |
| starch | 0.200 g |
| precipitated silica | 0.036 g |
| magnesium stearate | 0.004 g |

We claim:

1. A substituted amide of the formula:

R—CONH—Het in which:
either (A) R denotes phenyl substituted by acyloxy, alkylthio or alkyloxycarbonylamino, by chlorine in the 2- or 4-position, or by two alkyloxy radicals, or R denotes a heterocyclic radical chosen from 2-pyridyl, 4-pyridyl, pyrazinyl, 5,6-dihydrodithiin-2-yl, 5,6-dihydrooxathiin-2-yl, 1,3-dithiolyl and thiazolyl, or thienyl or furyl substituted by halogen or by alkythio, or R denotes alkenyl of 2 to 4 carbon atoms in which the double bond is in the α-position with respect to the carbonyl group of the amide function, and Het denotes 1,8-naphthyridin-2-yl substituted at the 7-position by halogen, alkyloxy, phenoxy, 3-chlorophenoxy, dichlorophenoxy, hydroxy or cyano, or (B) R denotes methoxyphenyl and Het denotes 1,8-naphthyridin-2-yl substituted at the 7-position with 3-chlorophenoxy, dichlorophenoxy, hydroxy or cyano, or (C) R denotes methoxy-3-pyridazinyl and Het denotes 1,8-naphthyridin-2-yl substituted at the 7-position by phenoxy, the said alkyl and acyl radicals mentioned above containing 1 to 4 carbon atoms each in a linear or branched chain.

2. An amide according to claim 1, in which R denotes phenyl substituted by acyloxy, alkylthio or alkyloxycarbonylamino, by chlorine in the 2- or 4-position or by 2 alkyloxy radicals, or R denotes 2-pyridyl, 4-pyridyl, pyrazinyl, 5,6-dihydrodithiin-2-yl, 5,6-dihydrooxathiin-2-yl, 1,3-dithiolyl, thiazolyl, 2-thienyl or 2-furyl substituted by halogen in the 5-position, or 5-alkylthio-2-thienyl, or R denotes alkenyl of 2 to 4 carbon atoms in which the double bond is in the α-position relative to the carbonyl group of the amide function, and Het denotes 1,8-naphthyridin-2-yl substituted at the 7-position by halogen, alkyloxy or phenoxy; or R denotes methoxyphenyl and Het denotes 1,8-naphthyridin-2-yl substituted at the 7-position by 3-chlorophenoxy, 3,4-dichlorophenoxy, hydroxy or cyano; or R denotes 6-methoxy-3-pyridazinyl and Het denotes 1,8-naphthyridin-2-yl substituted at the 7-position by phenoxy, the said alkyl and acyl radicals containing 1 to 3 carbon atoms each in a linear or branched chain.

3. An amide according to claim 1, in which either R denotes phenyl substituted by acyloxy, 5,6-dihydrodithiin-2-yl, 1,3-dithiolyl or 4-thiazolyl, and Het denotes a 1,8-naphthyridin-2-yl radical substituted at the 7-position by halogen or methoxy; or R denotes 4-methoxyphenyl and Het denotes 1,8-naphthyridin- 2-yl substituted at the 7-position by 3-chlorophenoxy or cyano.

4. An amide according to claim 1 which is N-(7-chloro-1, 8-naphthyridin-2-yl)-4-acetoxybenzamide.

5. An amide according to claim 1 which is N-(7-chloro-1,8-naphthyridin-2-yl)-3-acetoxybenzamide.

6. An amide according to claim 1 which is N-(7-methoxy-1,8-naphthyridin-2-yl)-3-acetoxybenzamide.

7. An amide according to claim 1 which is N-(7-chloro-1,8-naphthyridin-2-yl)-1,3-dithiole-4-carboxamide.

8. An amide according to claim 1 which is N-(7-cyano-1,8-naphthyridin-2-yl)-4-methoxybenzamide.

9. A pharmaceutical composition useful as an anxiolytic, hypnotic or muscle relaxant comprising, in combination with one or more compatible and pharmaceutically acceptable diluents or adjuvants, an effective amount of an amide of the formula R—CONH—Het in which: either (A) R denotes phenyl substituted by acyloxy, alkyithio or alkyloxycarbonylamino, by chlorine in the 2- or 4- position, or by two alkyloxy radicals, or R denotes a heterocyclic radical chosen from 2-pyridyl, 4-pyridyl, pyrazinyl, 5,6-dihydrodithiin-2-yl, 5,6-dihydrooxathiin-2-yl, 1,3-dithiolyl and thiazolyl, or thienyl or furyl substituted by halogen or by alkylthio, or R denotes alkeyl of 2 to 4 carbon atoms in which the double bond is in the alpha-position with respect to the carbonyl group of the amide function, and Het denotes 1,8-naphthyridin-2-yl substituted at the 7-position by halogen, alkyloxy, phenoxy, 3-chlorophenoxy, dichlorophenoxy, hydroxy or cyano, or (B) R denotes methoxyphenyl and Het denotes 1,8-naphthyridin-2-yl substituted at the 7-position with 3-chlorophenoxy, dichlorophenoxy, hydroxy or cyano, or (C) R denotes methoxy-3-pyridazinyl and Het denotes 1,8-naphthyridin-2-yl substituted at the 7-position by phenoxy, the said alkyl and acyl radicals mentioned above containing 1 to 4 carbon atoms each in a linear or branched chain.

10. A method of producing an anxiolytic, hypnotic, or muscle relaxant effect in a subject in which such effect is required which comprises administering to such subject an effective amount of an amide as claimed in claim 1.

* * * * *